(12) United States Patent
Tachibe et al.

(10) Patent No.: US 9,421,219 B2
(45) Date of Patent: Aug. 23, 2016

(54) METHODS AND COMPOSITIONS FOR PREVENTING ALLERGY AND INFECTION

(71) Applicant: Matsutani Chemical Industry Co., Ltd., Itami-shi, Hyogo (JP)

(72) Inventors: Makoto Tachibe, Itami (JP); Toyohide Nishibata, Itami (JP); Shozo Sugano, Itami (JP)

(73) Assignee: Matsutani Chemical Industry Co., Ltd., Itami-shi, Hyogo (JP)

( * ) Notice: Subject to any disclaimer, the term of this patent is extended or adjusted under 35 U.S.C. 154(b) by 367 days.

(21) Appl. No.: 13/777,084

(22) Filed: Feb. 26, 2013

(65) Prior Publication Data

US 2013/0230560 A1 Sep. 5, 2013

(30) Foreign Application Priority Data

Mar. 2, 2012 (JP) ................................. 2012-046768

(51) Int. Cl.
*A61K 39/395* (2006.01)
*A61K 31/718* (2006.01)

(52) U.S. Cl.
CPC .................................. *A61K 31/718* (2013.01)

(58) Field of Classification Search
None
See application file for complete search history.

(56) References Cited

U.S. PATENT DOCUMENTS

| 2006/0178343 | A1* | 8/2006 | Shimotoyodome et al. ... 514/60 |
| 2014/0065220 | A1* | 3/2014 | Tachifuji ...................... 424/489 |

FOREIGN PATENT DOCUMENTS

| CN | 1772295 A | 5/2006 |
| CN | 101032544 A | 9/2007 |
| JP | 01-242532 A | 9/1989 |
| JP | 02-280059 A | 11/1990 |
| JP | 04-342533 A | 11/1992 |
| JP | 05-339161 A | 12/1993 |
| JP | 06-032743 A | 2/1994 |
| JP | 06-234647 A | 8/1994 |
| JP | 11-092389 A | 4/1999 |
| JP | 2003-155249 A | 5/2003 |
| JP | 2003-201239 A | 7/2003 |
| JP | 2004-043326 A | 2/2004 |
| JP | 2004-256478 A | 9/2004 |
| JP | 2005-075740 A | 3/2005 |
| JP | 2005-082494 A | 3/2005 |
| JP | 2005-097133 A | 4/2005 |
| JP | 2005-179195 A | 7/2005 |
| JP | 2005-239571 A | 9/2005 |
| JP | 2005-255574 A | 9/2005 |
| JP | 2007-308419 A | 11/2007 |
| JP | 2011-116735 A | 6/2011 |
| JP | 2011-184300 A | 9/2011 |

* cited by examiner

*Primary Examiner* — Yunsoo Kim
(74) *Attorney, Agent, or Firm* — Foley & Lardner LLP

(57) ABSTRACT

To provide an IgA production promoter capable of being easily ingested safely and continually, for example orally and capable of preventing infection by inhibiting the binding of pathogenic microorganisms to alimentary canal mucosa and preventing an allergic reaction by blocking the passage of allergen materials such as pollen and house dust through the wall of the alimentary tract. The present invention consists of an IgA production promoter comprising hydroxypropyl starch as an effective ingredient. The IgA production promoter of the present invention can be safely and continually ingested because the effective ingredient thereof is hydroxypropyl starch used in food and the like, and can prevent infection by inhibiting the binding of pathogenic microorganisms to alimentary canal mucosa and prevent an allergic reaction by blocking the passage of allergen materials such as pollen and house dust through the wall of the alimentary tract.

2 Claims, 2 Drawing Sheets

Danet-test(*$p<0.05$,vs TS)

METHODS AND COMPOSITIONS FOR PREVENTING ALLERGY AND INFECTION

TECHNICAL FIELD

The present invention relates to an IgA production promoter comprising hydroxypropyl starch as an effective ingredient, and a method for promoting IgA production in a mammal comprising administering the hydroxypropyl starch as an effective ingredient orally to the mammal.

BACKGROUND ART

In an organism such as a mammal, the skin or the mucosa is at the interface with the external environment. The organism is in contact with pathogenic microorganisms, parasites, or many substances such as pathogenic antigens and food antigens at the interface with the external environment, and is exposed to the risk of the entry of harmful foreign materials into the organism by the contact. To prevent the entry of the foreign materials into the organism, the organism has the immune system, which protects the organism through the action of immunoglobulins.

Immunoglobulin A (IgA) is a type of immunoglobulin present in a mammal and is made up of 2 heavy chains (a chains) and 2 light chains (κ and λ chains). The IgA molecule has 2 antigen-binding sites; however, it forms a dimer by binding via a polypeptide called J chain and has antigen-binding sites in exocrine secretions in the respiratory tract, the intestinal tract, and the like. The dimeric IgA (secretory IgA) plays the leading role in mucosal immunity and functions as the front line of the immune mechanism in the alimentary tract and the respiratory apparatus. Secretory IgA is contained in the colostrum and operative to protect the alimentary tract of a newborn infant from bacterial/viral infection (fetomaternal immunity). The production quantity of IgA in humans is the second largest after IgG among various immunoglobulins. The molecular weight of the monomer is 160,000.

IgA is produced and secreted in the form of a dimer by IgA-producing plasma cells present in the lamina propria of an effector tissue. Thereafter, it is bound to a secreted component expressed on the basal membrane side of mucosal epithelial cells, incorporated into the epithelial cells, and secreted into the lumen side. The secreted component has a role in protecting IgA from degradation by proteinase, and the secretory IgA also has a function as a natural antibody against a dietary protein, a blood group substance, an normal inhabitant, or the like in addition to exhibiting antibody activities against various pathogenic viruses and bacteria. In other words, IgA prevents the entry of microorganisms into the mucosal surface via these systems to play an important role in the biological defense mechanism. Secretory IgA is highly resistant to degradation by enzymes, is not degraded even in the intestinal tract, and is also detected in feces.

In summary, IgA is useful in the prevention of the entry of pathogenic microorganisms or allergen substances from the small intestine, the nose, the bronchial mucosa, or the like and in the maintenance of homeostasis. Particularly, IgA present in the intestinal tract is known to contribute to protection against infection, prevention from the occurrence of allergy by foreign protein, or the like. In artificially fed infants fed on nursery dry milk containing no secretory IgA and patients with IgA deficiency, it is known that IgG against dietary antigen appears with high frequency and the degree of progress of the occurrence of allergic diseases or autoimmune diseases is high. Thus, increased IgA production is expected to contribute to protection against infection, prevention from the occurrence of allergy, or the like.

Various substances have conventionally been disclosed as those capable of promoting the in vivo production of IgA. Disclosed IgA production promoters using peptides as effective ingredients include, for example, an IgA production promoter consisting of a peptide selected from the group consisting of a peptide mixture obtained by hydrolysis of a lactoferrin, a peptide isolated from the peptide mixture, a chemically synthesized peptide, a pharmaceutically acceptable salt thereof, and a mixture thereof (Japanese unexamined Patent Application Publication No. 06-32743) and an IgA production promoter using a milk-derived milk fat globule membrane or a milk K-casein-derived glycomacropeptide as an effective ingredient (Japanese unexamined Patent Application Publication No. 05-339161).

Disclosed IgA production promoters using bacterial cells as an effective ingredient include, for example, an IgA production promoter using cells of *Bifidobacterium* breve or particular *Bifidobacterium* cells obtained from the search of cells having the ability to induce antibody as an effective ingredient (Japanese unexamined Patent Application Publication No. 01-242532 or 02-280059), an IgA production promoter using a protoplast or cytoplasmic membrane fraction of a bacterium belonging to the genus *Bifidobacterium* as an effective ingredient (Japanese unexamined Patent Application Publication No. 04-342533), and an IgA production promoter using a bacterial cell autolysate obtained by keeping a suspension of live cells of a bacterium belonging to the genus *Bifidobacterium* warm at 40 to 55° C. and pH 6 to 12 for 1 hour or more, as an effective ingredient (Japanese unexamined Patent Application Publication No. 06-234647). In addition, there are also disclosed an IgA production promoter using cells, killed cells, or cells lysed or crushed with chemical/enzymatic treatment or physical treatment, of a bacterium belonging to the genus *Enterococcus*, as an effective ingredient (Japanese unexamined Patent Application Publication No. 11-92389), and an IgA production promoter using a plant-derived lactic acid bacterium belonging to the genus *Lactobacillus* such as *Lactobacillus delbrueckii*, *Lactobacillus brevis*, *Lactobacillus sakei*, or *Lactobacillus curyatus* or a plant-derived lactic acid bacterium belonging to the genus *Pediococcus* such as *Pediococcus pentosaceus*, as an effective ingredient (Japanese unexamined Patent Application Publication No. 2007-308419). An IgA production promoter is also disclosed using phycocyanin protein pigment obtained by extraction and purification from a cyanobacterium such as spirulina, as an effective ingredient (Japanese unexamined Patent Application Publication No. 2004-256478).

Disclosed IgA production promoters using components derived from mushrooms as effective ingredients include, for example, an IgA production promoter using a Lentinus edodes mycelium extract as an effective ingredient (Japanese unexamined Patent Application Publication No. 2003-155249), an IgA production promoter using a fruit body of *Sparassis crispa* and/or a processed product thereof or a mycelium of *Sparassis crispa* and/or a processed product thereof as an effective ingredient (Japanese unexamined Patent Application Publication No. 2005-97133), and an IgA production promoter using an acidic sugar and an acidic peptide having average molecular weights of 5,000 to 10,000 (inclusive) extracted from a fruit body of Eumycota Thelephoraceae such as *Boletopsis leucomelas*, Shishitake, or *Sarcodon aspratus*, as effective ingredients (Japanese unexamined Patent Application Publication No. 2005-75740).

Disclosed IgA production promoters using plant-derived components as effective ingredients include, for example, an IgA production-leveling agent using a component consisting of a citrus fruit or its processed material, particularly preferably a compressed material or fruit rind of an Onsyu mandarin orange, as an effective ingredient (Japanese unexamined Patent Application Publication No. 2005-255574), an immunoglobulin (such as IgA) production promoter using aurapten obtained by use of the fruit rind of a citrus fruit as a raw material and extraction from the raw material of the citrus fruit using a solvent such as ethanol, methanol, hexane, ethyl acetate, or dimethyl sulfoxide (DMSO) and β-cryptoxanthin obtained by use of the pulp or the like of a citrus fruit as a raw material and extraction from the raw material of the citrus fruit using a solvent such as ethanol, methanol, hexane, or ethyl acetate, as an effective ingredient (Japanese unexamined Patent Application Publication No. 2011-116735), and an IgA production promoter using a component extracted from a plant such as *Anthriscus cerefolium*, *Calendula officinalis*, *Sambucus nigra*, or *Althaea officinalis*, as an effective ingredient (Japanese unexamined Patent Application Publication No. 2011-184300).

Disclosed IgA production promoters using sugar-related components as effective ingredients include, for example, a mucosa immunopotentiating composition enhancing the production of IgA and the like, using a fructo-oligosaccharide as an effective ingredient (Japanese unexamined Patent Application Publication No. 2003-201239), an immunoadjuvant using a phosphorylated saccharide in which a plurality of phosphate groups are bound per one glucan molecule such as cellulose, amylose, glycogen, starch, or dextrin, as an effective ingredient (Japanese unexamined Patent Application Publication No. 2004-43326 or 2005-82494), a secretory IgA production inducer using a cyclic inulooligosaccharide cyclofructan obtained by treating inulin, the main ingredient of a carbohydrate obtained from a root of Jerusalem artichoke, Cichorium intybus, or the like, with a cyclic inulooligosaccharide-producing enzyme, cycloinulooligosaccharide fructanotransferase, as an effective ingredient (Japanese unexamined Patent Application Publication No. 2005-179195), and an antibody production inducer for inducing the production of antibodies such as IgA, using a tea polysaccharide having a molecular weight of 10,000 or more, extracted from tea with water or hot water and containing galacturonic acid, galactose, and arabinose as constituent sugars, as an effective ingredient (Japanese unexamined Patent Application Publication No. 2005-239571).

As described above, various substances are disclosed as those promoting the production of IgA in vivo. However, it has not ever been known that a modified starch such as hydroxypropyl starch has the effect of promoting the production of IgA.

PRIOR ART DOCUMENTS

Patent Documents

[Patent Document 1] Japanese unexamined Patent Application Publication No. 01-242532
[Patent Document 2] Japanese unexamined Patent Application Publication No. 02-280059
[Patent Document 3] Japanese unexamined Patent Application Publication No. 04-342533
[Patent Document 4] Japanese unexamined Patent Application Publication No. 05-339161
[Patent Document 5] Japanese unexamined Patent Application Publication No. 06-32743
[Patent Document 6] Japanese unexamined Patent Application Publication No. 06-234647
[Patent Document 7] Japanese unexamined Patent Application Publication No. 11-92389
[Patent Document 8] Japanese unexamined Patent Application Publication No. 2003-155249
[Patent Document 9] Japanese unexamined Patent Application Publication No. 2003-201239
[Patent Document 10] Japanese unexamined Patent Application Publication No. 2004-43326
[Patent Document 11] Japanese unexamined Patent Application Publication No. 2004-256478
[Patent Document 12] Japanese unexamined Patent Application Publication No. 2005-75740
[Patent Document 13] Japanese unexamined Patent Application Publication No. 2005-82494
[Patent Document 14] Japanese unexamined Patent Application Publication No. 2005-97133
[Patent Document 15] Japanese unexamined Patent Application Publication No. 2005-179195
[Patent Document 16] Japanese unexamined Patent Application Publication No. 2005-255574
[Patent Document 17] Japanese unexamined Patent Application Publication No. 2005-239571
[Patent Document 18] Japanese unexamined Patent Application Publication No. 2007-308419
[Patent Document 19] Japanese unexamined Patent Application Publication No. 2011-116735
[Patent Document 20] Japanese unexamined Patent Application Publication No. 2011-184300

SUMMARY OF THE INVENTION

Object to be Solved by the Invention

An object of the present invention is to provide an IgA production promoter capable of being easily ingested safely and continually, for example, orally and capable of preventing infection by inhibiting the binding of pathogenic microorganisms to alimentary canal mucosa and preventing an allergic reaction by blocking the passage of allergen materials such as pollen and house dust through the wall of the alimentary tract.

Further, another object of the present invention is to provide a method for promoting IgA production in a mammal comprising administering the hydroxypropyl starch as an effective ingredient orally to the mammal.

Means to Solve the Object

To provide an IgA production promoter capable of being easily ingested safely and continually, for example, orally and capable of preventing pathogenic organism infection or an allergic reaction by blocking the binding of pathogenic microorganisms to alimentary canal mucosa or the passage of allergen materials and the like through the wall of the alimentary tract, in intensive search for the agent, the present inventors have found that hydroxypropyl starch used in food and the like has the effect of promoting the production/secretion of IgA in the small intestine of rats fed on a feed containing the hydroxypropyl starch, thereby accomplishing the present invention.

Thus, the present invention consists of an IgA production promoter comprising hydroxypropyl starch as an effective ingredient. In the IgA production promoter of the present invention, the hydroxypropyl starch as an effective ingredient preferably has a degree of substitution (DS) of the hydroxypropyl starch of 0.1 or more. The IgA production promoter of the present invention can be prepared into a dosage form for oral administration and orally administered. The IgA production promoter of the present invention can be safely and continually ingested because the effective ingredient thereof is hydroxypropyl starch used in food and the like, and can prevent infection by inhibiting the binding of pathogenic microorganisms to alimentary canal mucosa and prevent an allergic reaction by blocking the passage of allergen materials such as pollen and house dust through the wall of the alimentary tract.

Effect of the Invention

The present invention provides an IgA production promoter which is safe, can be orally ingested, and even can be continually ingested. The IgA production promoter of the present invention comprises hydroxypropyl starch used in food and the like as an effective ingredient, can safely and effectively prevent infection by inhibiting the binding of pathogenic microorganisms to alimentary canal mucosa, and can prevent an allergic reaction by blocking the passage of allergen materials and the like through the wall of the alimentary tract.

MODE OF CARRYING OUT THE INVENTION

Figure 1:
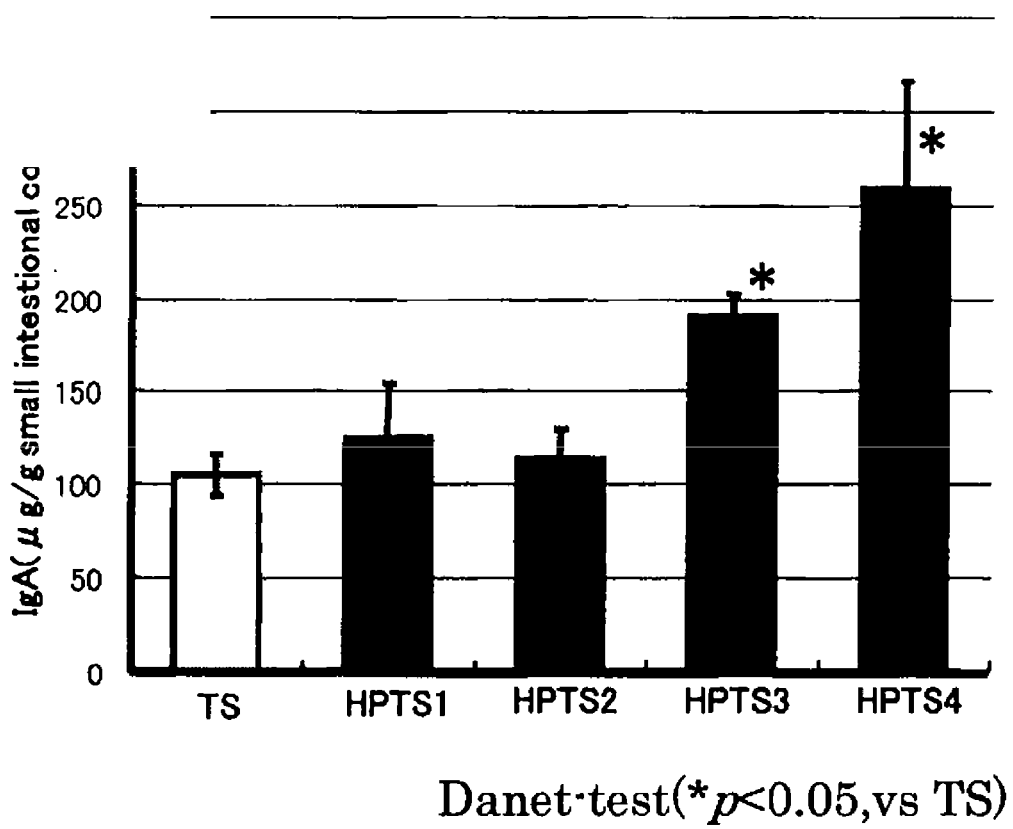
FIG. 1 is a graph showing the results of measurement of IgA in small intestine contents, for measuring IgA production in the small intestine in an experiment on the IgA production-promoting effect of hydroxypropyl starch using rats in Example of the present invention.

The present invention consists of an IgA production promoter comprising hydroxypropyl starch as an effective ingredient. The IgA production promoter according to the present invention is characterized by containing the hydroxypropylated starch produced by reacting starch with propylene oxide under alkali conditions, as an effective ingredient. The effective ingredient of the IgA production promoter of the present invention may be the hydroxypropylated phosphate-crosslinked starch obtained by combining a crosslinking reaction using phosphorus oxychloride or sodium trimetaphosphate in the hydroxypropylation reaction to prevent starch gelatinization, and includes a mandatory requirement for the ether linkage of hydroxypropyl groups to starch.

Further, the present invention also relates to a method for promoting IgA production in a mammal comprising administering the hydroxypropyl starch as an effective ingredient orally to the mammal.

The promotion of IgA production refers to a function which potentiates/activates the production of IgA and relatively increases the total amount of IgA in secreta and egesta. For example, when measured under the same conditions as those of a measuring method as described in an evaluation test in Example of the present specification, it means that the ingestion of the IgA production promoter is evaluated to make IgA into an increased state compared to normal. As a method for measuring the amount of IgA production, a kit such as IgA ELISA Quantitation Kit (Cosmo Bio Co., Ltd.) or Salivary EIA Kit (Funakoshi Co., Ltd.) is commercially available, and can be used to measure the amount of IgA production.

The raw material starch for the hydroxypropyl starch of the present invention is not particularly limited; however, it is selected, for example, from wheat, tapioca, high-amylose corn, potato, corn, sago, bean, waxy corn, waxy potato, rice, and glutinous rice, and one or more of these can be used. Particularly preferred examples of the starch include tapioca starch and waxy corn starch.

The hydroxypropyl starch of the present invention is obtained by hydroxypropylating the above raw material starch by a conventional method. On this occasion, the method may be used in combination with any one or more of processings such as crosslinking treatment, pregelatinization treatment, acid treatment, alkali treatment, roasting treatment, enzyme treatment. For the degree of hydroxypropylation, a high DS is preferable and a DS of 0.1 or more is more preferable.

The method for producing the hydroxypropyl starch is not particularly limited, and it can be produced according to an ordinary method. For example, water is added to starch to make about 30 to 40% by weight of a slurry, to which a starch swelling inhibitor such as dietary salt or sodium sulfate is then added, followed by reaction with propylene oxide at 35 to 45° C. using alkali (e.g., caustic soda) as a catalyst. DS is regulated by the addition amount of propylene oxide. The hydroxypropyl starch of the present invention may be one hydroxypropylated substantially to the above DS, and combination with other processing methods as described above may be used. Here, the pregelatinization treatment, the crosslinking treatment, the acid treatment, the alkali treatment, the roasting treatment, the enzyme treatment, and the like may be all performed according to an ordinary method.

The IgA production promoter of the present invention is characterized by containing hydroxypropyl starch as an effective ingredient, and may be hydroxypropyl starch itself; however, it may contain other ingredients, for example, various starches, processed starches, starch degradation products, saccharides, sugar alcohols, or soybean polysaccharides, and may be used in combination with a water-soluble dietary fiber material such as non-digestible dextrin or polydextrose, an insoluble dietary fiber material such as cellulose, a commercially available resistant starch (RS) material, or the like. It may also contain a sweetener, a coloring agent, a preservative, a thickening stabilizer, an antioxidant, a gum base, a spice, a bittering agent, an enzyme, a brightener, an acidulant, a seasoning, an emulsifier, gluten, a nutrient supplement for nutritional enhancement, and the like. The blending ratio should be set considering the amount of prescription, the addition amount, and a subject for ingestion in ingesting the IgA production promoter or eating a food produced and cooked by blending the IgA production promoter; although the hydroxypropyl starch as an effective ingredient can exert an effect even when ingested in a small amount, the blending ratio is preferably set so that it is preferably ingested at 5 g, more preferably 10 g/day/normal adult.

The IgA production promoter of the present invention obtained by the above method can be made into various dosage forms. For example, when orally administered as a pharmaceutical preparation, it can be made into, but not limited to, tablets, capsules, powders, granules, pills, liquids, emulsions, suspensions, solutions, spirits, syrups, extracts, and elixirs. Its formulation can also contain various pharmaceutically acceptable carriers. For example, it can contain but not limited to an excipient, a binder, a disintegrant, a lubricant, a flavoring agent, a coloring agent, a sweetener, a corrigent, a solubilizer, a suspending agent, an emulsifier, and a coating agent. The IgA production promoter of the present invention may be made into a sustained or controlled release formulation.

The IgA production promoter of the present invention can be ingested by blending in a food or drink to which a processed starch is known to be applied. Examples thereof include blending in bakery products, noodles, snack foods such as okonomiyaki (a Japanese pizza-like food), takoyaki (octopus balls), or a hot cake, Japanese confectionery, batter for pastes or fried foods, fritters, yoghurt, purines, jellies, dressings including mayonnaise and sauce, ankake (kudzu sauce), ices such as ice cream, meat products, cooked rice, imitation rice, and various drinks such as powdered drinks, soft drinks, carbonated drinks, soft yoghurt, and jelly drink, and blending in bakery products, noodles, and jelly drink is preferable.

When used as a feed, the IgA production promoter of the present invention may be administered by blending in a known feed for livestock or pet animals, or is entirely satisfactorily administered directly. It can also be supplied as a premix.

The effect of the IgA production promoter of the present invention will be illustrated below with reference to Example. However, the present invention is not intended to be limited thereto.

EXAMPLES

Experimental Example

Four tapioca starch slurries containing sodium sulfate were prepared, and propylene oxide was properly added thereto under alkali conditions, followed by reaction for 20 hours. The resultant liquids were washed with water, dried, and pulverized to provide four hydroxypropyl starches having different DS (Table 1).

TABLE 1

| Sample | DS | Remark |
|---|---|---|
| HPTS1 | 0.058 | Comparative Example 1 |
| HPTS2 | 0.086 | Comparative Example 2 |
| HPTS3 | 0.14 | Example 1 |
| HPTS4 | 0.34 | Example 2 |

Example 1

Test Method

Wistar rats (7-week old) were divided into 5 groups at n=6 and fed for 4 weeks on feeds containing the samples prepared in Experimental Example, using tapioca starch (TS) as a control (Table 2: Feed Blending). 24-Hour feces were collected at each of 3 days during the period of testing and stored at −80° C. The three days' feces were pooled to make a feces sample. After 6 hours of fasting, dissection was performed to recover small intestine contents. The amount of IgA was measured for the small intestine contents and each feces sample together with the evaluation of variation in body weight, the feed ingestion amount, and the amount of ingested energy. Rat IgA ELISA Quantitation Set (Bethyl Laboratories, Inc., Montgomery, Tex., USA) was used for the measurement of IgA.

<Result>

Figure 2:
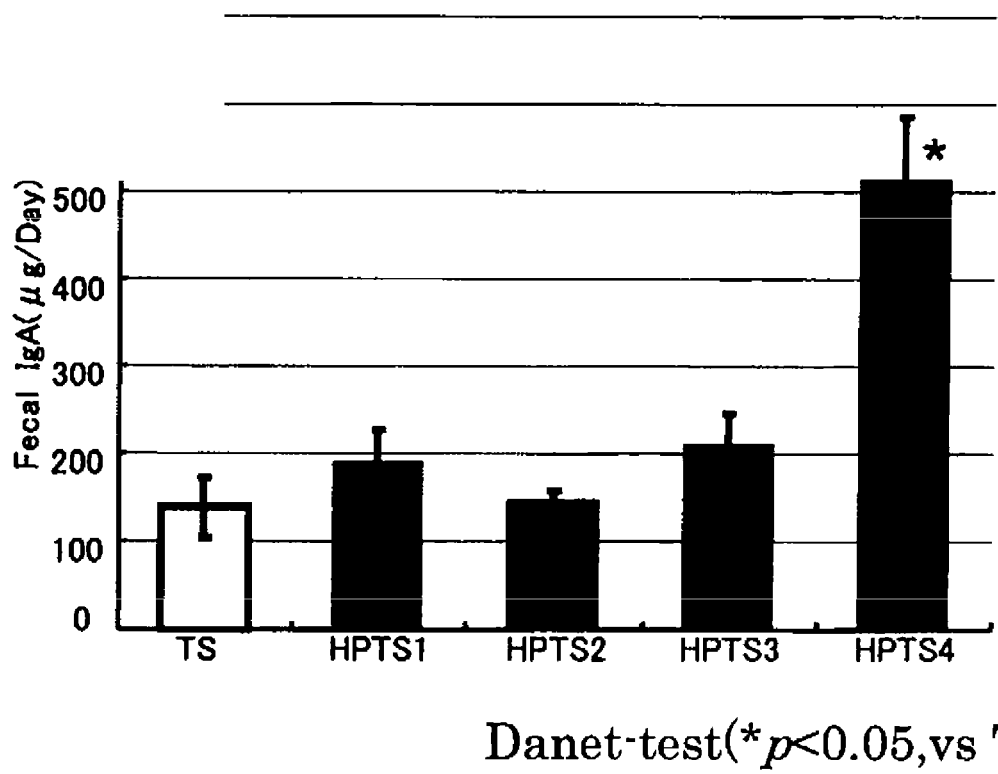
FIG. 2 is a graph showing the results of measurement of IgA in feces, for measuring IgA production in the small intestine in an experiment on the IgA production-promoting effect of hydroxypropyl starch using rats in Example of the present invention.

The evaluation of variation in body weight, the feed ingestion amount, and the amount of ingested energy showed no significant differences in both Comparative Examples and Examples, and no difference was observed in appetite and growth. On the other hand, the amount of IgA in small intestine contents significantly increased in rats fed on the feed containing each of HPTS3 and HPTS4 used in Examples 1 and 2 (FIG. 1). IgA in the feces also significantly increased in Example 2 (FIG. 2). These results show that hydroxypropyl starch is useful as an IgA production promoter. In other words, the IgA production promoter of the present invention can promote the production/secretion of IgA without impeding appetite or growth.

TABLE 2

| Ingredients | Control (AIN-93G) | HPTS | | | |
|---|---|---|---|---|---|
| (g/kg) | TS | HPTS1 | HPTS2 | HPTS3 | HPTS4 |
| Casein | 200 | 200 | 200 | 200 | 200 |
| α-Tapioka strach | 532 | 532 | 532 | 532 | 532 |
| Sucrose | 100 | 100 | 100 | 100 | 100 |
| Soybean oil | 70 | 70 | 70 | 70 | 70 |
| HPTS1 | — | 50 | — | — | — |
| HPTS2 | — | — | 50 | — | — |
| HPTS3 | — | — | — | 50 | — |
| HPTS4 | — | — | — | — | 50 |
| Cellulose | 50 | 50 | 50 | 50 | 50 |
| AIN93 mineral mixture | 35 | 35 | 35 | 35 | 35 |
| AIN93 vitamin mixture | 10 | 10 | 10 | 10 | 10 |
| L-Cystine | 3 | 3 | 3 | 3 | 3 |
| Total | 1000 | 1000 | 1000 | 1000 | 1000 |

INDUSTRIAL APPLICABILITY

The present invention provides an IgA production promoter which is safe, can be orally ingested, and even can be continually ingested. The IgA production promoter of the present invention comprises hydroxypropyl starch used in food and the like as an effective ingredient, can safely and effectively prevent infection by inhibiting the binding of pathogenic microorganisms to alimentary canal mucosa and can also prevent an allergic reaction by blocking the passage of allergen materials and the like through the wall of the alimentary tract.

The invention claimed is:

1. A method for promoting IgA production in an intestinal tract of a mammal comprising orally administering a hydroxypropyl starch having a degree of hydroxypropylation of 0.1 or higher as an effective ingredient to the mammal in need thereof at a dose of 5 g or more per day per normal adult.

2. The method according to claim 1, wherein the hydroxypropyl starch is prepared into a dosage form, having a degree of hydroxypropylation of at least 0.3 as an effective ingredient for oral administration.

* * * * *